US011593638B2

(12) United States Patent
Kezurer et al.

(10) Patent No.: US 11,593,638 B2
(45) Date of Patent: Feb. 28, 2023

(54) SYSTEM AND METHOD FOR ORIENTATING CAPTURE OF ULTRASOUND IMAGES

(71) Applicants: New York University, New York, NY (US); Yeda Research And Development Co. Ltd., Rechovot (IL)

(72) Inventors: Itay Kezurer, Rechovot (IL); Yoram Eshel, Netanya (IL); Achiau Ludomirsky, New York, NY (US); Yaron Lipman, Kibbutz Netzer Sereni (IL)

(73) Assignees: New York University, New York, NY (US); Yeda Research And Development Co. Ltd, Rehovot (IL)

( * ) Notice: Subject to any disclaimer, the term of this patent is extended or adjusted under 35 U.S.C. 154(b) by 919 days.

(21) Appl. No.: 16/412,675

(22) Filed: May 15, 2019

(65) Prior Publication Data

US 2019/0354856 A1    Nov. 21, 2019

Related U.S. Application Data

(60) Provisional application No. 62/671,692, filed on May 15, 2018.

(51) Int. Cl.
*G06N 3/08* (2006.01)
*G06T 7/00* (2017.01)
(Continued)

(52) U.S. Cl.
CPC ............ *G06N 3/08* (2013.01); *A61B 5/7267* (2013.01); *A61B 8/13* (2013.01); *A61B 8/4254* (2013.01);
(Continued)

(58) Field of Classification Search
CPC ..... A61B 5/7267; A61B 8/0833; A61B 8/085; A61B 8/0883; A61B 8/13; A61B 8/14;
(Continued)

(56) References Cited

U.S. PATENT DOCUMENTS

2009/0221896 A1    9/2009 Rickert
2012/0065510 A1    3/2012 Snare et al.
(Continued)

FOREIGN PATENT DOCUMENTS

JP    2016168142    9/2016
WO    2014099825    6/2014
(Continued)

OTHER PUBLICATIONS

International Search Report for corresponding PCT application PCT/US2019/32368 dated Sep. 17, 2019.
(Continued)

*Primary Examiner* — Amelie R Davis
(74) *Attorney, Agent, or Firm* — Heidi Brun Associates Ltd.

(57) ABSTRACT

A downloadable navigator for a mobile ultrasound unit having an ultrasound probe, implemented on a portable computing device. The navigator includes a trained orientation neural network to receive a non-canonical image of a body part from the mobile ultrasound unit and to generate a transformation associated with the non-canonical image, the transformation transforming from a position and rotation associated with a canonical image to a position and rotation associated with the non-canonical image; and a result converter to convert the transformation into orientation instructions for a user of the probe and to provide and display the orientation instructions to the user to change the position and rotation of the probe.

24 Claims, 9 Drawing Sheets

(51) Int. Cl.
| | |
|---|---|
| *A61B 8/00* | (2006.01) |
| *G06T 3/20* | (2006.01) |
| *G06T 11/00* | (2006.01) |
| *G16H 30/40* | (2018.01) |
| *A61B 5/00* | (2006.01) |
| *A61B 8/13* | (2006.01) |
| *G09B 23/28* | (2006.01) |
| *G06T 3/60* | (2006.01) |

(52) U.S. Cl.
CPC ............ *A61B 8/4427* (2013.01); *A61B 8/463* (2013.01); *G06T 3/20* (2013.01); *G06T 3/60* (2013.01); *G06T 7/0012* (2013.01); *G06T 11/003* (2013.01); *G09B 23/286* (2013.01); *G16H 30/40* (2018.01); *G06T 2207/10132* (2013.01); *G06T 2207/20081* (2013.01); *G06T 2207/20084* (2013.01); *G06T 2207/30048* (2013.01)

(58) Field of Classification Search
CPC ... A61B 8/4245; A61B 8/4254; A61B 8/4427; A61B 8/461; A61B 8/463; A61B 8/466; A61B 8/467; A61B 8/483; A61B 8/54; A61B 8/58; A61B 8/585; G06N 3/08; G06T 1/20; G06T 11/003; G06T 2207/10132; G06T 2207/20081; G06T 2207/20084; G06T 2207/30048; G06T 3/20; G06T 3/60; G06T 7/0012
See application file for complete search history.

(56) References Cited

U.S. PATENT DOCUMENTS

| | | | |
|---|---|---|---|
| 2013/0070993 A1* | 3/2013 | Baek | A61B 8/5261 382/131 |
| 2014/0148808 A1 | 5/2014 | Inkpen | |
| 2014/0180177 A1 | 6/2014 | Rothberg et al. | |
| 2015/0310581 A1 | 10/2015 | Radulescu et al. | |
| 2016/0143627 A1 | 5/2016 | Vignon et al. | |
| 2016/0155050 A1 | 6/2016 | Buibas | |
| 2017/0213112 A1 | 7/2017 | Sachs et al. | |
| 2017/0262382 A1 | 9/2017 | Patoulatos et al. | |
| 2018/0153505 A1 | 6/2018 | Cadieu et al. | |

FOREIGN PATENT DOCUMENTS

| | | |
|---|---|---|
| WO | 2016176198 A | 11/2016 |
| WO | 20180136805 | 7/2018 |

OTHER PUBLICATIONS

Extended European Search Report issued in corresponding European application 19803070.2 dated Oct. 8, 2021.
1 Search Report for corresponding Russian application 2020139165 dated Jun. 8, 2022.

* cited by examiner

SYSTEM AND METHOD FOR ORIENTATING CAPTURE OF ULTRASOUND IMAGES

CROSS REFERENCE TO RELATED APPLICATIONS

This application claims priority from U.S. provisional patent application 62/671,692, filed May 15, 2018, which is incorporated herein by reference.

FIELD OF THE INVENTION

The present invention relates to mobile handheld ultrasound machines generally and to orientation for correct use in particular.

BACKGROUND OF THE INVENTION

A medical ultrasound (also known as diagnostic sonography or ultrasonography) is a diagnostic imaging technique based on the application of an ultrasound. It is used to create an image of internal body structures such as tendons, muscles, joints, blood vessels and internal organs.

Acquiring accurate images in order to perform an effective examination and diagnosis requires placing the ultrasound transducer in an angular position in space with the pertinent organ or body part, as is illustrated in FIG. 1 to which reference is now made. FIG. 1 shows an ultrasound image of an organ of interest 12 taken with a transducer 14. It will be appreciated that the art of navigating transducer 14 to the exact angular position required to achieve the optimal or "canonical" image of organ 12 is crucial to the success of the ultrasound examination. The process typically requires a trained and skilled sonographer.

For example, in order to perform an echocardiogram, the sonographer has to take images of the heart from various canonical directions, such as four-chamber and two-chamber views. The correct positioning of the transducer is crucial to receiving the optimal view of the left ventricle and consequently to extract the functional information of the heart.

Mobile ultrasound machines or devices are known in the art, such as the Lumify commercially available from Philips. These mobile ultrasound machines are available in the form of a transducer that communicates with a program downloadable to any portable handheld device such as a smart phone or a tablet.

The availability of such devices means that ultrasounds may be performed off-site (away from hospitals, etc.) for example, as a triage tool for ambulances or even in the battlefield, at urgent care facilities, nursing homes, etc. without requiring bulky expensive equipment.

SUMMARY OF THE PRESENT INVENTION

There is provided, in accordance with a preferred embodiment of the present invention, a downloadable navigator for a mobile ultrasound unit having an ultrasound probe, implemented on a portable computing device. The navigator includes a trained orientation neural network to receive a non-canonical image of a body part from the mobile ultrasound unit and to generate a transformation associated with the non-canonical image, the transformation transforming from a position and rotation associated with a canonical image to a position and rotation associated with the non-canonical image; and a result converter to convert the transformation into orientation instructions for a user of the probe and to provide and display the orientation instructions to the user to change the position and rotation of the probe.

Moreover, in accordance with a preferred embodiment of the present invention, the navigator also includes a trainer to train the orientation neural network using the canonical image together with non-canonical images taken around the canonical image and transformations to positions and rotations in space associated with the non-canonical images from the canonical image.

Further, in accordance with a preferred embodiment of the present invention, the trainer includes a training converter to receive IMU (inertia measurement unit) data during training sessions from an IMU mounted on a training probe, the IMU data providing the positions and rotations associated with the non-canonical images and the canonical image, and to convert the positions and rotations to transformations from the position and rotation associated with the canonical image to the position and rotation associated with the non-canonical images.

Still further, in accordance with a preferred embodiment of the present invention, the trainer includes an untrained orientation neural network and a loss function to train the untrained orientation neural network, the loss function to reduce a distance between a calculated transformation produced by the untrained orientation neural network and a ground truth transformation for each non-canonical image.

Additionally, in accordance with a preferred embodiment of the present invention, the loss function additionally includes a probability to constrain the calculated transformation to one of a plurality of different canonical orientations.

Moreover, in accordance with a preferred embodiment of the present invention, the canonical image is one of a plurality of canonical images.

Further, in accordance with a preferred embodiment of the present invention, the navigator includes a diagnoser to make a diagnosis from a final image generated by the probe when viewing the canonical image.

Still further, in accordance with a preferred embodiment of the present invention, the portable computing device is one of: a smartphone, a tablet, a laptop, a personal computer, and a smart appliance.

Additionally, in accordance with a preferred embodiment of the present invention, the navigator includes a set creator to receive a multiplicity of transformations from the trained orientation neural network in response to images from the probe and to generate sets of images and their associated transformations; a sufficiency checker to determine when enough sets have been created; and a trained cyclical canonical view neural network to generate a set of summary cyclical canonical images showing changes in the body part during a body part cycle.

Moreover, in accordance with a preferred embodiment of the present invention, the navigator includes a cyclical canonical view trainer to train an untrained cyclical canonical view neural network with the sets of images, their associated transformations, and their associated summary cyclical canonical images at each point in the body cycle.

Further, in accordance with a preferred embodiment of the present invention, the body part cycle is a cardiac cycle.

Still further, in accordance with a preferred embodiment of the present invention, each set has a single element therein.

There is provided, in accordance with a preferred embodiment of the present invention, a navigator for a mobile ultrasound unit implemented on a portable computing device having an ultrasound probe. The navigator includes a trained orientation neural network to provide orientation information for a multiplicity of ultrasound images captured around a body part, the orientation information to orient the image with respect to a canonical view of the body part; and a volume reconstructer to orientate the images according to the orientation information, to generate a volume representation of the body part from the oriented images using tomographic reconstruction and to generate a canonical image of the canonical view from the volume representation.

Moreover, in accordance with a preferred embodiment of the present invention, the navigator includes a sufficiency checker to receive orientations from the trained orientation neural network in response to images from the probe and to determine when enough images have been received; and a result converter to request further images for the trained orientation neural network in response to the sufficiency checker.

Further, in accordance with a preferred embodiment of the present invention, the navigator includes diagnoser to make a diagnosis from the volume representation of the body part.

There is provided, in accordance with a preferred embodiment of the present invention, a navigator for a mobile ultrasound unit having an ultrasound probe, implemented on a mobile device. The navigator includes a trained mapping neural network to receive a non-canonical image of a body part from the probe, to map the non-canonical image to a non-canonical map point on a displayable map and to map a multiplicity of canonical images associated with the non-canonical image to canonical map points on the displayable map; and a result converter to display the map marked with canonical and non-canonical map points.

Moreover, in accordance with a preferred embodiment of the present invention, the trained mapping neural network includes a loss function to ensure that changes in the motion of the probe generate small motions on the displayable map, that distances between images be similar to the distance between map locations and that optimal paths between one canonical image to another be straight, constant speed trajectories.

Further, in accordance with a preferred embodiment of the present invention, the navigator also includes a diagnoser to make a diagnosis from a final image generated by the probe when a user moves the probe to one of the canonical map points.

There is provided, in accordance with a preferred embodiment of the present invention, a downloadable navigator for a mobile ultrasound unit having an ultrasound probe, implemented on a mobile device. The navigator includes a set creator to receive images from the probe over time and to generate sets of images; a sufficiency checker to determine when enough sets have been generated; and a cyclical canonical view neural network to generate a set of summary cyclical canonical images showing changes in the body part during a body part cycle.

Moreover, in accordance with a preferred embodiment of the present invention, the navigator also includes a diagnoser to make a diagnosis from a final image generated by the cyclical canonical view neural network.

There is provided, in accordance with a preferred embodiment of the present invention, a method for a mobile ultrasound unit having an ultrasound probe, implemented on a portable computing device, the method includes receiving, using a trained orientation neural network, a non-canonical image of a body part from the mobile ultrasound unit and generating a transformation associated with the non-canonical image, the transformation transforming from a position and rotation associated with a canonical image to a position and rotation associated with the non-canonical image; and converting the transformation into orientation instructions for a user of the probe and providing and displaying the orientation instructions to the user to change the position and rotation of the probe.

Moreover, in accordance with a preferred embodiment of the present invention, the method includes training the orientation neural network using the canonical image together with non-canonical images taken around the canonical image and transformations to positions and rotations in space associated with the non-canonical images from the canonical image.

Further, in accordance with a preferred embodiment of the present invention, the training includes receiving IMU (inertia measurement unit) data during training sessions from an IMU mounted on a training probe, the IMU data providing the positions and rotations associated with the non-canonical images and the canonical image, and converting the positions and rotations to transformations from the position and rotation associated with the canonical image to the position and rotation associated with the non-canonical images.

Still further, in accordance with a preferred embodiment of the present invention, the trained mapping neural network includes a loss function to ensure that changes in the motion of the probe generate small motions on the displayable map, that distances between images be similar to the distance between map locations and that optimal paths between one canonical image to another be straight, constant speed trajectories.

Additionally, in accordance with a preferred embodiment of the present invention, the loss function additionally includes a probability to constrain the calculated transformation to one of a plurality of different canonical orientations.

Moreover, in accordance with a preferred embodiment of the present invention, the canonical image is one of a plurality of canonical images.

Further, in accordance with a preferred embodiment of the present invention, the method includes making a diagnosis from a final image generated by the probe when viewing the canonical image.

Still further, in accordance with a preferred embodiment of the present invention, the portable computing device is one of: a smartphone, a tablet, a laptop, a personal computer, and a smart appliance.

Additionally, in accordance with a preferred embodiment of the present invention, the method also includes receiving a multiplicity of transformations from the trained orientation neural network in response to images from the probe and generating sets of images and their associated transformations; determining when enough sets have been created; and generating, using a trained cyclical canonical view neural network, a set of summary cyclical canonical images showing changes in the body part during a body part cycle.

Moreover, in accordance with a preferred embodiment of the present invention, the method also includes training an untrained cyclical canonical view neural network with the sets of images, their associated transformations, and their associated summary cyclical canonical images at each point in the body cycle.

Further, in accordance with a preferred embodiment of the present invention, the body part cycle is a cardiac cycle.

Still further, in accordance with a preferred embodiment of the present invention, each set has a single element therein.

There is provided, in accordance with a preferred embodiment of the present invention, a method for a mobile ultrasound unit implemented on a portable computing device having an ultrasound probe, the method includes providing, using a trained orientation neural network, orientation information for a multiplicity of ultrasound images captured around a body part, the orientation information to orient the image with respect to a canonical view of the body part; and the images according to the orientation information, generating a volume representation of the body part from the oriented images using tomographic reconstruction and generating a canonical image of the canonical view from the volume representation.

Moreover, in accordance with a preferred embodiment of the present invention, the method includes receiving orientations from the trained orientation neural network in response to images from the probe and determining when enough images have been received; and requesting further images for the trained orientation neural network in response to the receiving orientations.

Further, in accordance with a preferred embodiment of the present invention, the method also includes making a diagnosis from the volume representation of the body part.

There is provided, in accordance with a preferred embodiment of the present invention, a method for a mobile ultrasound unit having an ultrasound probe, implemented on a mobile device. The method includes receiving using a trained mapping neural network, a non-canonical image of a body part from the probe, mapping the non-canonical image to a non-canonical map point on a displayable map and mapping a multiplicity of canonical images associated with the non-canonical image to canonical map points on the displayable map; and displaying the map marked with canonical and non-canonical map points.

Moreover, in accordance with a preferred embodiment of the present invention, the trained mapping neural network includes a loss function to ensure that changes in the motion of the probe generate small motions on the displayable map, that distances between images are be similar to the straight, constant speed trajectories.

Further, in accordance with a preferred embodiment of the present invention, the method also includes making a diagnosis from a final image generated by the probe when a user moves the probe to one of the canonical map points.

There is provided, in accordance with a preferred embodiment of the present invention, a method for a mobile ultrasound unit having an ultrasound probe, implemented on a mobile device. The method includes receiving images from the probe over time and generating sets of images; determining when enough sets have been generated; and generating via a cyclical canonical view neural network, a set of summary cyclical canonical images showing changes in the body part during a body part cycle.

Moreover, in accordance with a preferred embodiment of the present invention, the method includes making a diagnosis from a final image generated by the cyclical canonical view neural network.

BRIEF DESCRIPTION OF THE DRAWINGS

The subject matter regarded as the invention is particularly pointed out and distinctly claimed in the concluding portion of the specification. The invention, however, both as to organization and method of operation, together with objects, images, and advantages thereof, may best be understood by reference to the following detailed description when read with the accompanying drawings in which:

Figure 1:
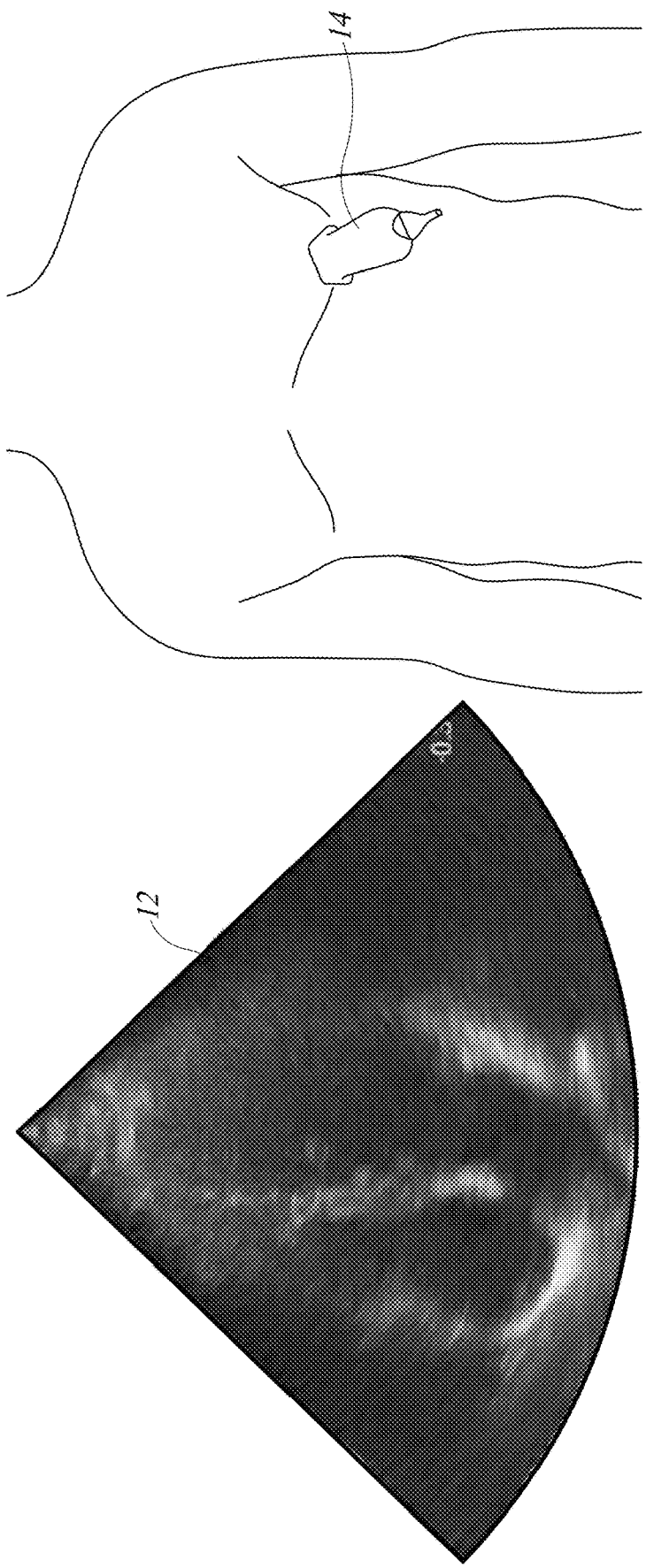
FIG. 1 is a schematic illustration of how an ultrasound transducer is placed to capture an image of a body part.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Applicants have realized that the ability to use mobile ultrasound machines away from conventional places such as hospitals, means that untrained sonographers or non-sonographers might utilize these machines. However, untrained doctors, first aid providers or even patients themselves do not have the training or knowledge to administer these ultrasounds correctly. It will be appreciated that a different training is required for different organs and body parts.

Prior art systems such as that described in US Patent Publication No. US2018/0153505 entitled "Guided Navigation of an Ultrasound Probe", published Jun. 7, 2018, and US Patent Publication No. US2016/0143627 entitled "Ultrasound Acquisition Feedback Guidance to a Target View", published May 26, 2016, teach methodologies for determining the deviations between a supplied image and a preferred canonical image of a particular body part for helping the non-sonographer guide his or her transducer to the optimal orientation for capturing a best fit image.

Applicants have realized that these prior art systems do not provide a complete solution vis-a-vis rotation calculations. Applicants have also realized that these prior art systems are not particularly useful, since they require additional hardware (such as inertial measurement units such as magnetometers, gyroscopes, accelerometers etc.) to aid in determining the location of the non-sonographer's probe. Applicants have realized that a system which does not require additional hardware and which is easily accessible, such as via a download in order to be integrated or used as an overlay with the processing software of the pertinent mobile ultrasound machine, is far more usable. As a result, the present invention operates only with the digital images generated by the ultrasound unit.

Figure 2:
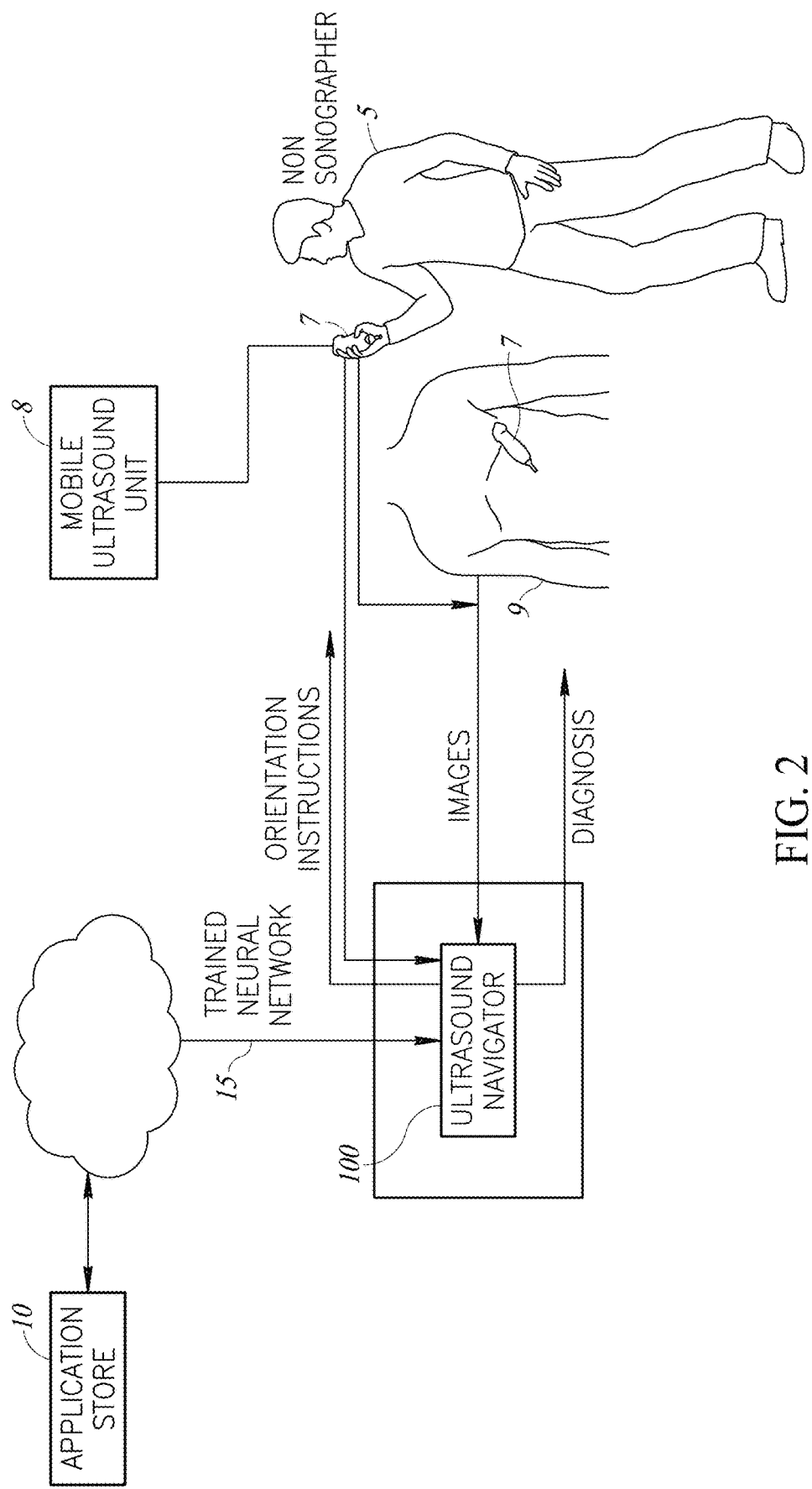
FIG. 2 is a schematic illustration of an ultrasound navigator; constructed and operative in accordance with the present invention.

Reference is now made to FIG. 2 which illustrates an ultrasound navigator 100, according to a first embodiment of the present invention, which may be downloaded from a mobile application store 10, such as the Appstore of Apple or Google Play of Google, onto any portable computing device, such as a smartphone, a tablet, a laptop, a personal computer, a smart appliance, etc.

It will be appreciated that navigator 100 may comprise (as part of the download) a trained orientation neural network 15. Orientation neural network 15 is described in more detail herein below. As discussed herein above, navigator 100 may integrated or used as an overlay with processing software of the pertinent mobile ultrasound machine Thus a user 5 may use a transducer or probe 7 (associated with mobile ultrasound unit 8) on patient 9 to supply images of a pertinent body part to navigator 100 and navigator 100 may supply orientation instructions accordingly as to how to orientate probe 7. It will be appreciated that the process may be iterative, with a non-sonographer or user 5 making more than one attempt to correctly orientate probe 7 in order to receive a suitable image. In accordance with a preferred embodiment of the present invention, "orientation" instructions may comprise both position (location in two or three-dimensional space) and rotation information (rotation in 3D space), even though navigator 100 receives only images.

Figure 3A:
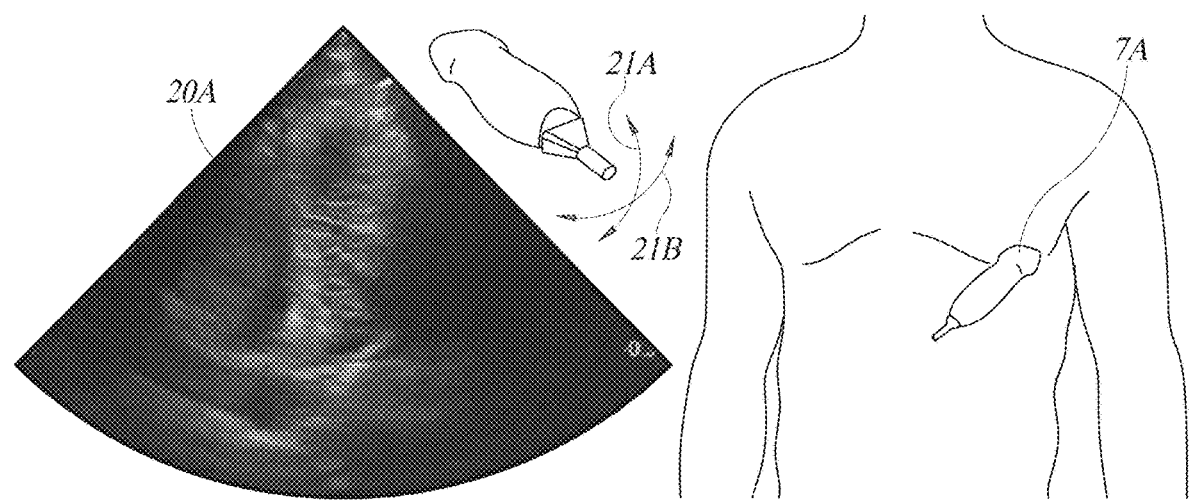
FIGS. 3A and 3B are schematic illustrations of how the navigator of FIG. 2 may aid a non-sonographer orientate probe a transducer in order to capture a suitable image of a body part, constructed and operative in accordance with the present invention.
Figure 3B:
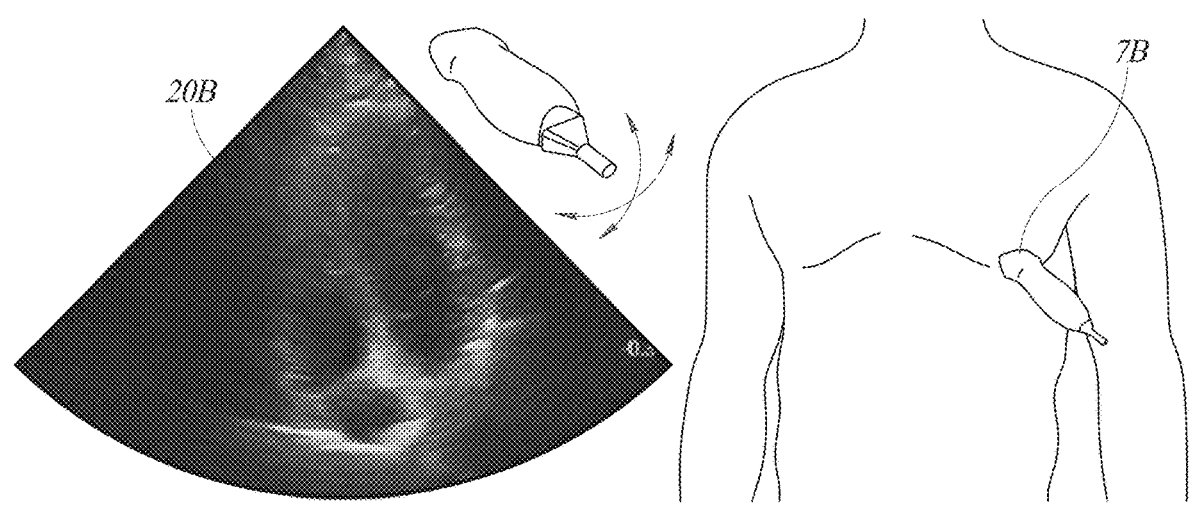

Reference is now made to FIGS. 3A and 3B which illustrate how navigator 100 may aid non-sonographer 5 to orientate probe 7 in order to capture a good image of a particular body part. FIG. 3A shows probe 7, labeled 7A, in the wrong position, i.e. the resultant image, labeled 20A, is not canonical. FIG. 3A additionally includes a set of arrows 21 instructing user 5 to change the rotation of probe 7A. Arrows 21A indicate a 'pitch up' kind of rotation. FIG. 3B shows probe 7B in the newly pitched US orientation and the resultant image 20B, which is better, though still not providing a canonical image. Arrows 21B indicate a new "yaw" rotation may be useful.

As discussed herein above, navigator 100 receives orientation neural network 15 which may be trained with expert data taken by a skilled sonographer for a particular body part or organ of interest. The training data received may include the canonical image of a particular body part as well as associated non-canonical images and for each, the orientation (i.e. position and rotation) of the sonographer's probe in space. It will be appreciated that this information may be generated using a probe with which an IMU (an inertial measurement unit which may include a magnetometer, a gyroscope, an accelerometer, etc.) is associated. The IMU may determine the orientation of the probe when an image is captured.

Figure 4:
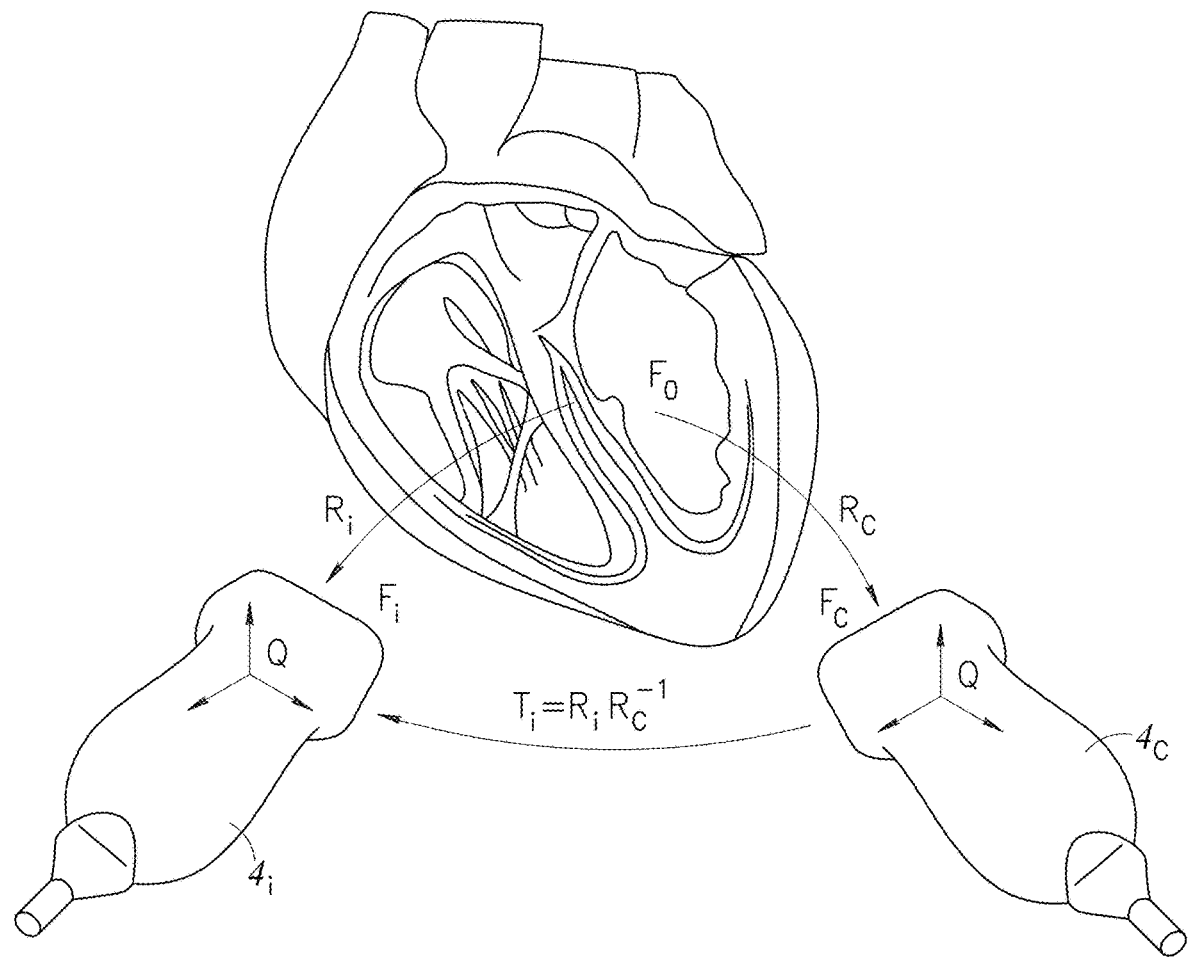
FIG. 4 is a schematic illustration of the transformation between the orientation of a training probe for a non-canonical image of an organ and its associated canonical image, constructed and operative in accordance with the present invention.

Reference is now made to FIG. 4 which illustrates the transformation between the orientation of a training probe 4c used by a trained sonographer for capturing the canonical image in relation to its orientation when capturing a non-canonical image for an organ. The orientation of training probe $4i$ when viewing the $i^{th}$ non-canonical image may be defined as a "frame of reference" $F_i$ in space where frame of reference $F_i$ may have the six degrees of freedom (6DoF), corresponding to a three axis system (Q) having three rotations around the axes and three translations along the axes, that an IMU may measure.

Frames of reference $F_i$ may refer to frame of reference at an origin O, where, for the present invention, the origin may be at the organ and its frame of reference in space may be defined as $F_o$. For each frame of reference $F_i$, there may be a transformation $R_i$ from the origin O, where the transformation $R_c$ may be a transformation to the desired orientation, labeled $F_c$, for viewing the canonical image, as follows:

$$R_c = F_c F_o^{-1}$$

$$R_i = F_i F_o^{-1} \quad (1)$$

where $F_o^{-1}$ is the inverse transform of $F_O$. Thus, a transformation $T_i$ from the canonical pose to the ith non-canonical pose may be $R_i R_c^{-1}$:

$$T_i = R_i R_c^{-1} = F_i F_0^{-1} (F_c F_c^{-1}) = F_i F_c^{-1} \quad (2)$$

Figure 5:
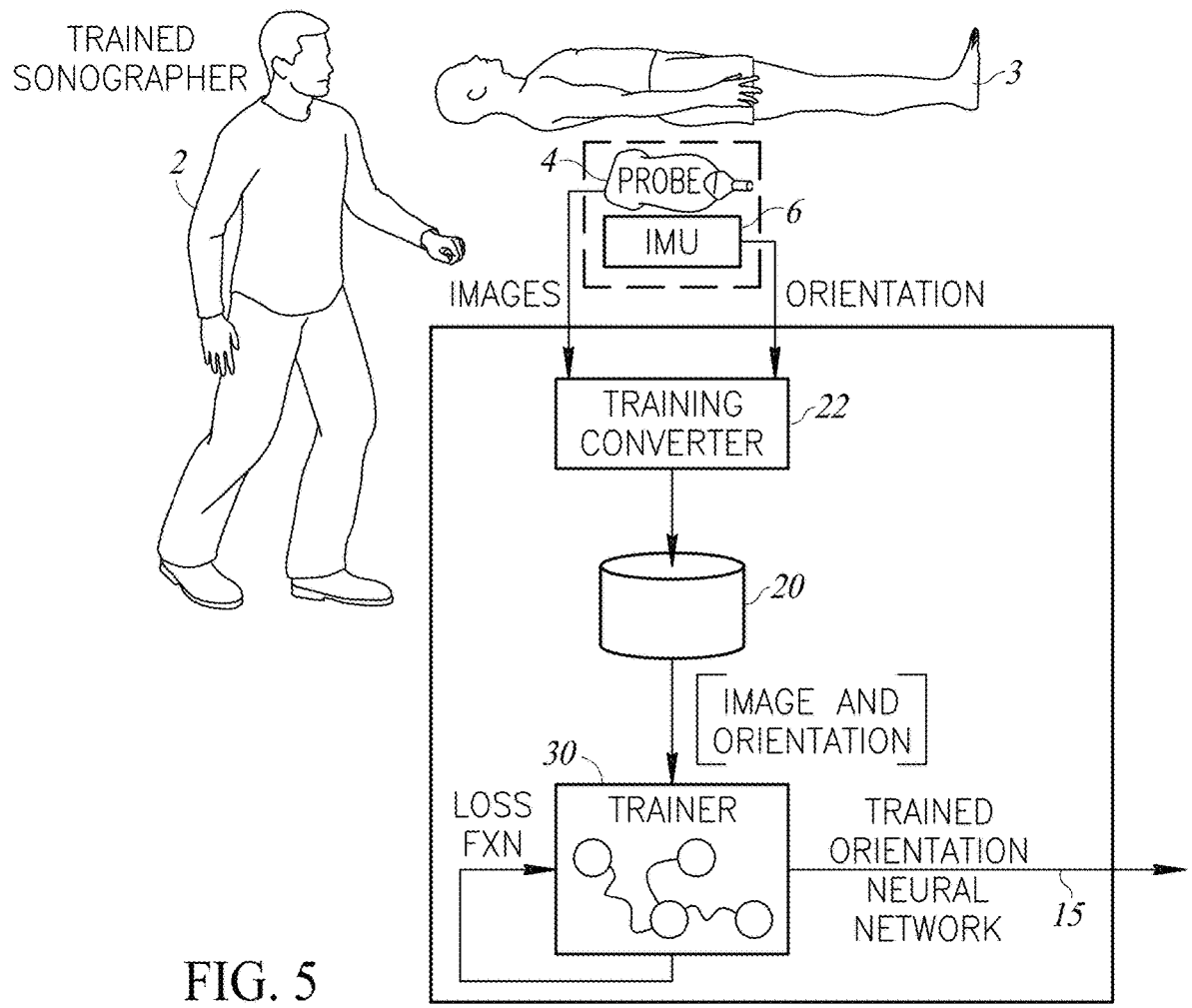
FIG. 5 is a schematic illustration of the training process for an orientation neural network, constructed and operative in accordance with the present invention.

Reference is now made to FIG. 5 which illustrates the training process for orientation neural network 15 using a trainer 30. A skilled sonographer 2 using training probe 4 on a patient 3 may provide both canonical and associated non-canonical images for a particular body part. It will be appreciated that training probe 4 may be associated with an IMU 6 (an inertial measurement unit which may include a magnetometer, a gyroscope, an accelerometer, etc.) which may determine the orientation $F_i$ of the probe when an image is captured.

Training converter 22 may receive the orientation data $F_i$ for each image and may determine the transformation $T_i = R_i R_c^{-1}$ from the associated canonical position, as discussed herein above with respect to FIG. 4. Specifically, training converter 22 may take images X from training probe 4 and may process them as necessary. Database 20 may store non-canonical images $X_i$ together with their orientation data $F_i$ and their transformation data $T_i$. Database 20 may also store canonical images $X_c$ and their associated orientation data $F_c$. It will be appreciated that there may be multiple canonical images for a body part. For example, the heart has a four chamber canonical image, a two chamber canonical image, etc., and thus, training converter 22 may generate the transformation $T_i$ to each relevant canonical image. It will be appreciated that the relevant canonical image may be provided manually or determined automatically by any suitable algorithm.

It will be appreciated that the incoming training data to trainer 30 may be a combination of image $X_i$ and its associated ground truth transformation $T_i$. For each non-canonical image, trainer 30 may learn the positioning transformation for the probe 4 to transform from viewing each canonical image to viewing each non-canonical image. It will be appreciated that the incoming data may comprise data from many different patients 3 so that trainer 30 may learn the changes in images $X_i$, possibly due to the sex, age, weight, etc., of patient 3 and any other factors which may influence the transformation information between the non-canonical images and the canonical image.

It will be further appreciated that trainer 30 may be any suitable neural network trainer, such as a convolutional neural network trainer, which may train the network by updating the network to minimize an energy "loss" as determined by a loss function such as a distance between a calculated transformation $S(X_i)$ produced by orientation neural network 15 and the ground truth transformation $T_i$ for image $X_i$ from its associated canonical image. It will be appreciated that transformation $S(X_i)$ begins as an untrained neural network and finishes as a trained neural network.

The distance function may be any suitable distance function. If there is more than one associated canonical image, orientation neural network 15 may be trained with the ground truth transformation $T_i$ to each non-canonical image. A loss function "Loss" may be calculated as:

$$\text{Loss} = \text{loss}(S(X_i), T_i) \tag{3}$$

Once orientation neural network 15 is trained, it may generate a transformation T for user probe 7 in response to each incoming image $X_i$. This transformation may then be inverted or converted to guide user 5 from the orientation for the non-canonical image to the orientation for the canonical image, as described in more detail herein below.

Figure 6:
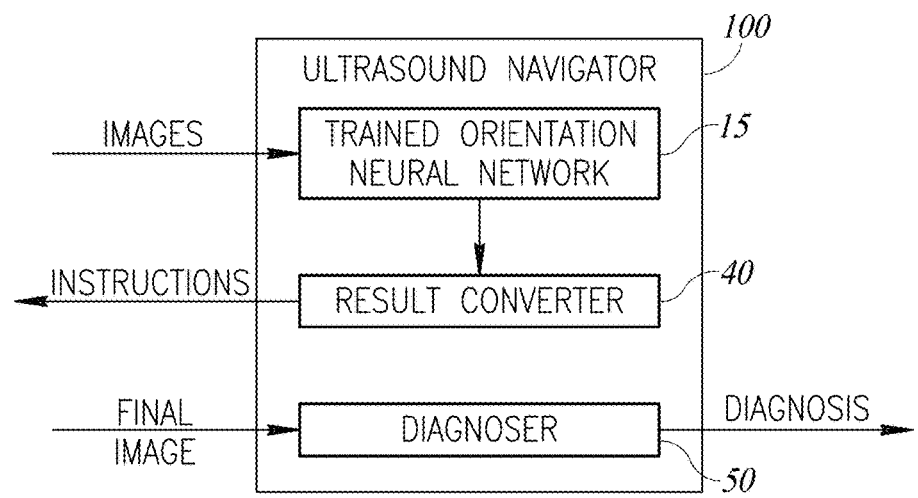
FIG. 6 is a schematic illustration of the elements of the navigator of FIG. 2, constructed and operative in accordance with the present invention.

Reference is now made to FIG. 6 which illustrates the components of navigator 100. Navigator 100 may comprise trained orientation neural network 15, a result converter 40 and a diagnoser 50.

As discussed herein above, user 5 may randomly place user probe 7 in relation to the desired body part. Trained orientation neural network 15 may provide the transformation T from the associated canonical image to the current non-canonical image of a particular body part. Result converter 40 may invert the generated transformation to provide orientation instructions for probe 7 from the current position and rotation viewing a non-canonical image to a position and rotation to view the associated canonical image. Result converter 40 may provide and display these orientation instructions to user 5 in various ways. It will be appreciated that this process may be iterative until user 5 positions probe 7 correctly (within an error range).

Result converter 40 may convert the orientation data S(X) produced by trained orientation neural network 15 into an explainable orientation for user 5, for a selected canonical image. Any suitable display may be utilized. An exemplary display is shown hereinabove with reference to FIGS. 3A and 3B. It will be appreciated that result converter 40 may use any appropriate interface and may (for example) display colored rotation markings. Moreover, result converter 40 may include elements that enable user 5 to indicate, when there are multiple canonical images for the body part, which canonical image is currently of interest.

Diagnoser 50 may receive the final canonical image produced by user 5 and may detect any anomalies therein. Diagnoser 50 may be any suitable diagnoser. For example, diagnose 50 may implement the diagnosis method of PCT International Publication WO 2018/136805, published 26 Jul. 2018, assigned to the common assignees of the present invention, and incorporated herein by reference.

Applicants have realized that the fact that there are multiple canonical images for a single body part and the fact that there are standard, known motions from one canonical image to another may be utilized to reduce errors in the output of trained orientation neural network 15.

In this improved embodiment, orientation neural network 15 may be trained to the multiple canonical images. Thus, for each image $X_i$, there may be multiple calculated transformations. For example, for a pair of canonical images c and c', there may be a pair of calculated transformations $S_c(X_i)$ and $S_{c'}(X_i)$ for the same image $X_i$ which may have associated ground truth transformations $T_{c,i}$ and $T_{c',i}$.

Moreover, there is a known motion transformation $T_k$ defined as:

$$T_k = R_c R_{c'}^{-1} \tag{4}$$

where $R_c$ is for canonical image c and $R_{c'}$ is for canonical image c'. These known motions are roughly constant across different subjects and therefore the transformation $T_k$ from one canonical image c to another c' may be utilized to constrain the calculated transformations $S_c(X_i)$ and $S_{c'}(X_i)$ to one of the canonical orientations. To do so, a probability measure $P_k$ may be used to define a maximum likelihood loss term $\log P_k(S_c(X_i) S_{c'}(X_i)^{-1})$ to add to the loss used to train orientation neural network 15, as follows:

$$\text{Loss} = \text{loss}(S_c(X_i), T_{c,i}) + \text{loss}(S_{c'}(X_i), T_{c',i}) - \delta^* \log P_k(S_c(X_i) S_{c'}(X_i)^{-1}) \tag{5}$$

The probability measure $P_k$ may be determined experimentally by measuring the ground truth transformation $T_k$ between canonical pose c and c' across different subjects. Moreover, there may be multiple probability measures per body part, one for each pair of canonical images for the body part, and each probability measure $P_k$ may define a separate additional term for the loss function.

Figure 7:
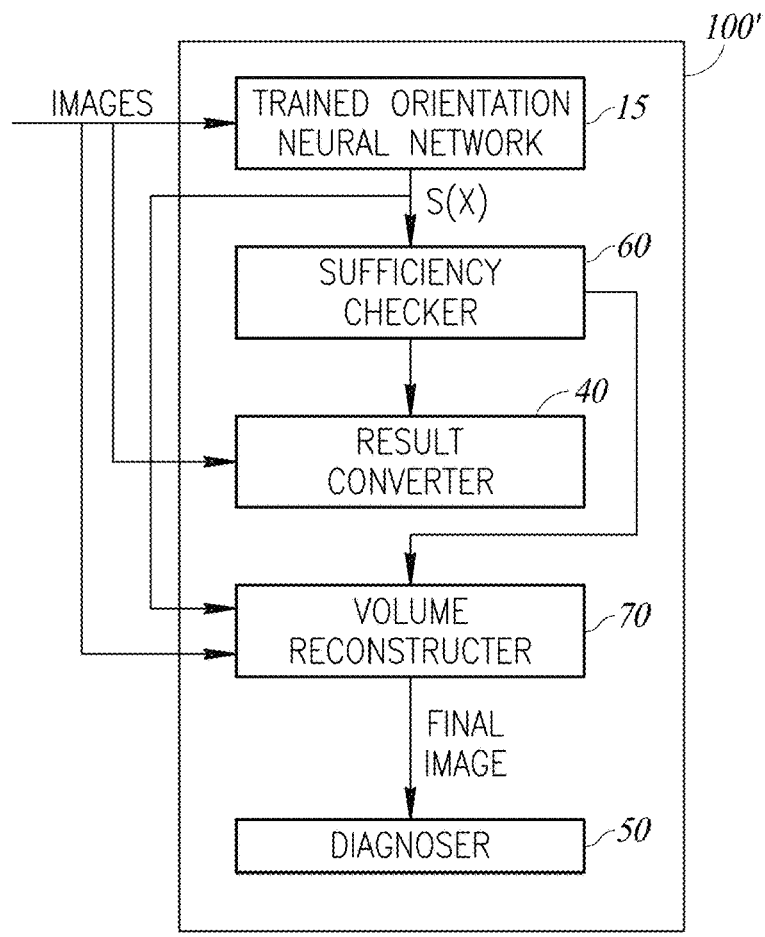
FIG. 7 is a schematic illustration of the elements of an alternative embodiment to the navigator of FIG. 2, constructed and operative in accordance with the present invention.

In an alternative embodiment, the navigator, here labeled 100', may also comprise a sufficiency checker 60 and a volume reconstructer 70, as is illustrated in FIG. 7. to which reference is now made.

Volume reconstructer 70 may utilize the output of trained orientation neural network 15 and may produce 3D or 4D functions, and/or 3D volumes or 3D space-time volumes of the body parts of interest from the images $X_i$ produced by probe 7. In this embodiment, the images $X_i$ may be considered as cross-sections of the body part of interest.

Sufficiency checker 60 may check that sufficient cross sections have been received via trained orientation neural network 15 in order to perform the 3D/4D volume reconstruction and may guide user 5 (via result converter 40) accordingly. For example, sufficiency checker 60 may determine when a pre-defined minimal number of images have been taken.

Upon an indication from sufficiency checker 60, volume reconstructer 70 may generate the 3D/4D volume, after which, reconstructer 70 may pull the relevant canonical views from the generated volume and may provide them to diagnoser 50. It will be appreciated that the canonical views in this embodiment are produced from the generated volume and may or may not have been among the images used to produce the volume.

Volume reconstructer 70 may utilize tomographic reconstruction, such as that based on inverse Radon transformation or other means, to reconstruct the 3D/4D functions and/or volumes from the images. It will be appreciated that for successful volumatic tomographic reconstruction, it is crucial to know the cross-section's position in 3D space or 4D space-time. Applicants have realized that trained orientation neural network 15 may provide a suggested transformation S(X) for probe 7 for each image taken and that transformation S(X) may be used to rotate the pixels of image $X_i$ from a fixed 2D imaging plane to the 3D orientation Q in space in which probe 4, was positioned when it produced image $X_i$.

Volume reconstructer 70 may receive the transformation $S(X_i)$ from trained orientation neural network 15 for each image $X_i$ and may apply the transformation to move the image from an imaging plane (as output from the probe) to a plane defined by the transformation of the probe, producing a rotated cross-section $CS_i$ of the body part. Volume reconstructer 70 may then use tomographic reconstruction to build the volume of the body part of interest from the images cross-sections $CS(X_i)$.

To apply transformation $S(X_i)$, it will first be appreciated that image $X_i$ comprises a set of pixels having a 2D location $(x_j, y_j)$ within the 2D imaging plane and an intensity $I_j$. Volume reconstructer 70 may apply transformation $S(X_i)$ on a 3D pixel location $(x_j, y_j, 0)$ in space to generate an approximation of the 3D orientation Q of image $X_i$ after which it may apply an operator H to center or scale the orientated image $X_i$, as follows:

$$Q = H*S(X_i)*[x_j, y_j, 0]^T \qquad (6)$$

Volume reconstructer 70 may provide the generated canonical image to diagnoser 50 which may then produce a diagnosis from it, as described hereinabove.

Figure 8A:
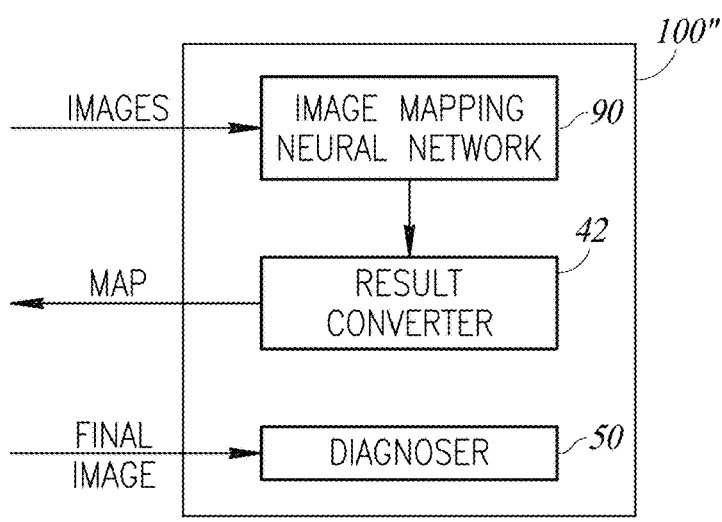
FIGS. 8A, 8B and 8C are schematic illustrations of the elements and function of an alternative embodiment to the navigator of FIG. 2, constructed and operative in accordance with the present invention.
Figure 8B:
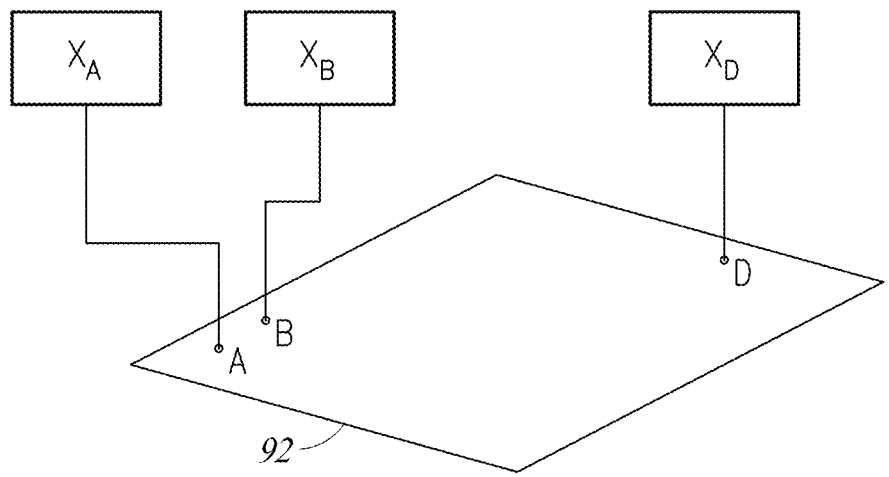
Figure 8C:
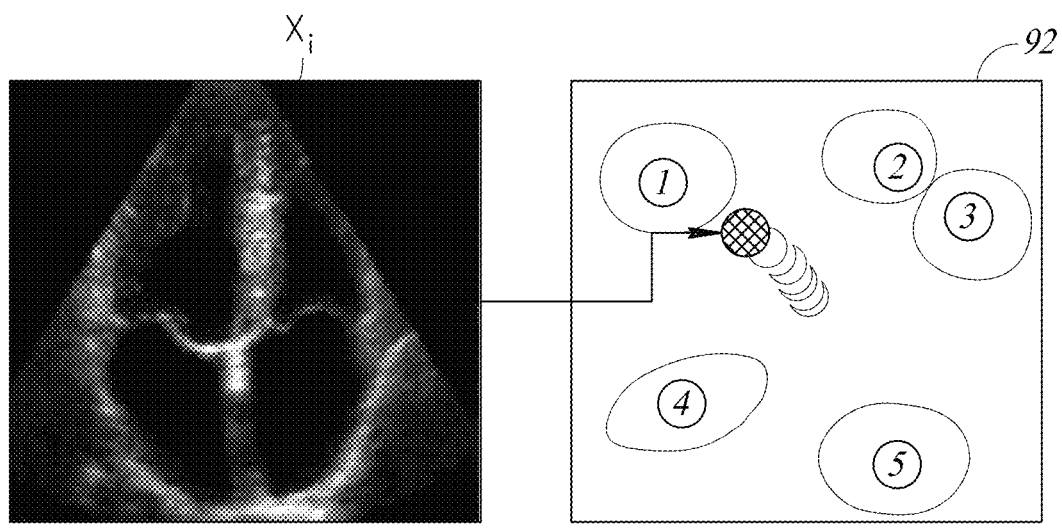

In yet another embodiment, illustrated in FIGS. 8A, 8B and 8C to which reference is now made, navigator, here labeled 100", may comprise an image mapping neural network 90. Mapping neural network 90 may map each image $X_i$ onto a 2D plane 92 (FIG. 8B). FIG. 8B shows three exemplary images $X_A$, $X_B$ and $X_D$ being mapped to three different locations A, B and D on plane 92.

Result converter, here labeled 42, may display 2D plane 92 to user 5, marking his current location in one color (for example, as a grey dot (shown in FIG. 8C as a shaded dot)) and the location of the canonical images for this body part as dots of other colors (shown in FIG. 8C as numbered circles 1-5). FIG. 8C also shows the acquired image $X_i$ and its map 92. Map point $M(X_i)$ may represent non-canonical image $X_i$ on map 92 and the other numbered circles may be canonical map points representing the desired or required canonical views c. User 5 may use trial and error movements of probe 7 to move map point $M(X_i)$ nearer towards the desired circles and mapper 90 may regenerate 2D plane 92 for each new image i from probe 7.

Applicants have realized that small changes in the motion of probe 7 should generate small motions on 2D plane 92 and that distances between images $X_i$ should be similar to the distance between map locations. Applicants have further realized that optimal paths from one canonical image to another should be straight, constant speed trajectories.

It will be appreciated that for this embodiment, mapping neural network 90 may be trained using incoming data which may include each image $X_i$ and the image $X_c$ of its associated canonical view.

Mapping neural network 90 may incorporate a loss function to minimize a distance between a calculated map point $M(X_i)$ currently produced by neural network 90 during training and the associated map point $M(X_c)$ for each canonical view $c_j$:

$$\text{Loss} = \text{loss}(M(X_i), M(X_{cj})) \qquad (7)$$

To incorporate an optimal path to the different canonical views, a probability vector $p_{i,j}$ may be added which may define how close the image $X_i$ is on a path to the jth desired canonical image c. The loss function may then be updated to be:

$$\text{Loss} = \text{loss}(M(X_i), \Sigma p_{i,j} M(X_{cj})) \qquad (8)$$

To preserve distances, the loss function may be updated to be:

$$\text{Loss} = \text{loss}(M(X_i), \Sigma p_{i,j} M(X_{cj})) + \text{loss}(\text{dist}(X_i, X_j), \|M(X_i) - M(X_j)\|_2) \qquad (9)$$

It will be appreciated that plane 92 may be either a 2D plane or a 3D volume, as desired. The mapping operations discussed herein above are operative for mapping to a 3D volume as well.

Applicants have realized that neural networks can be trained not just to generate transformation information but to generate canonical images, given the right kind of training. This might be particularly useful if the input from non-sonographers is expected to be noisy (since they may not have steady enough hands) and/or if it is desired to see, at the canonical view, the body part functioning. For example, ultrasound sonographers regularly provide information about a full cardiac cycle, from systole to distole and back to systole, for cardiac function analysis.

Figure 9A:
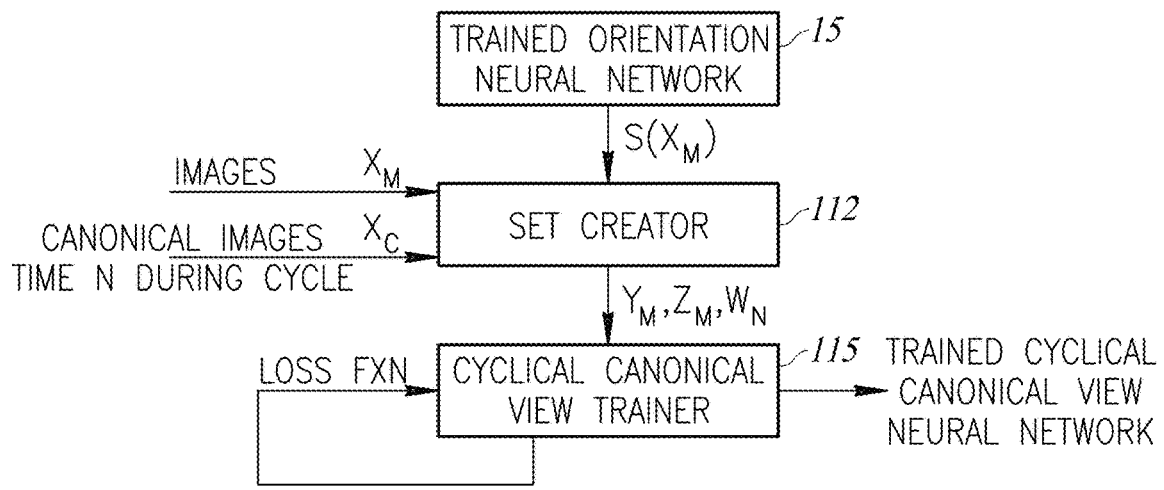
FIGS. 9A and 9B are schematic illustrations of the elements of an alternative embodiment to the navigator of FIG. 2 at training and in operation, constructed and operative in accordance with the present invention.
Figure 9B:
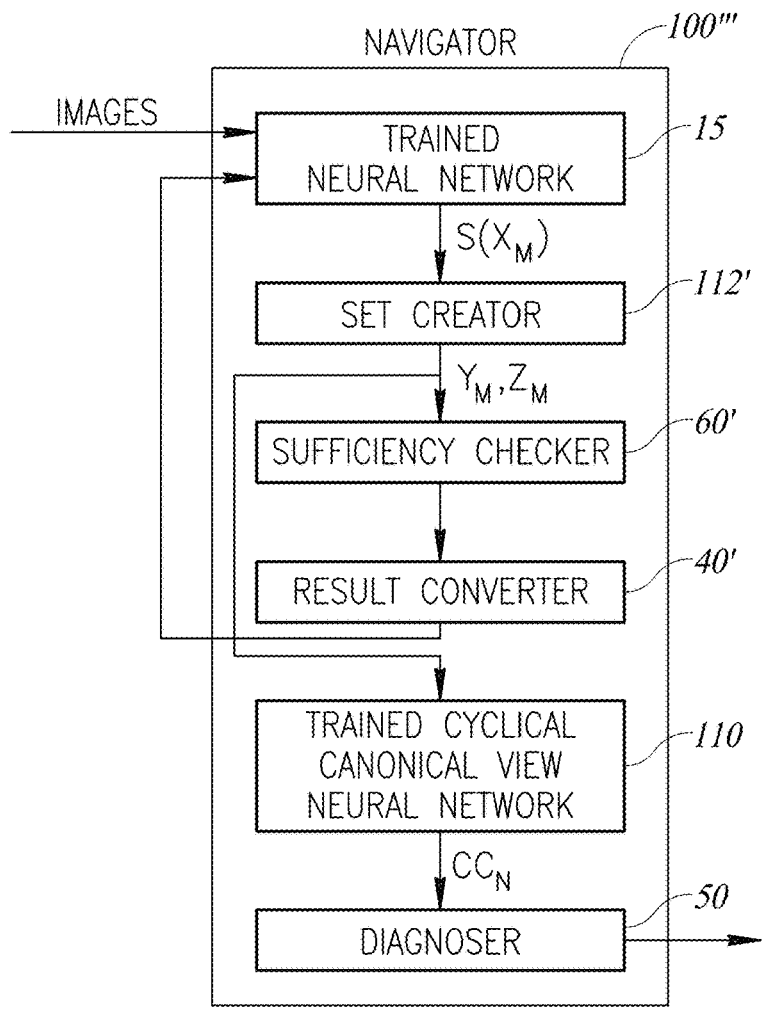

In yet another embodiment, shown in FIGS. 9A and 9B to which reference is now made, navigator 100 may comprise a cyclical canonical view neural network 110, which may be a neural network trained from the output of trained orientation neural network 15. Canonical view cycler 110 may aggregate repeating images to reduce noise and to provide a less noisy summarization of (for example) an organ cycle, such as the cardiac cycle.

As shown in FIG. 9A, the elements needed for training cyclical canonical view neural network 110 may comprise trained orientation neural network 15, a set creator 112 to create the input to network 110, and a cyclical canonical view trainer 115.

For this embodiment, skilled sonographer 2 may provide multiple ultrasound images m taken over time as well as multiple images n taken over time at one canonical view pose c. Set creator 112 may receive image $X_m$ from trained orientation neural network 15 along with its associated transformation information $S(X_m)$ and may combine these with their associated image $X_{c,n}$ taken at the canonical view. Skilled sonographer 2 may provide such associations.

Set creator 112 may then generate triplets $\{[Y_m, Z_m], W_n\}$ where $[Y_m, Z_m]$ are input to cyclical canonical view trainer 115 and $W_n$ is the associated output. Each $Y_m$ may consist of a set of g images where $Y_m = \{X_1, X_2, \ldots, X_g\}$ and $Z_m$ may consist of the transformation information $S(X)$ of the images $Y_m$ such that $Z_m = \{S(X_1), S(X_2), \ldots, S(X_g)\}$. Typically, g may be 10-100 images.

Each pair $[Y_m, Z_m]$ may have a set $W_n$ of associated canonical images $X_c$ taken at the canonical view c at times between 0 and n. The time n may indicate the time within the cardiac cycle. As mentioned herein above, skilled sonographer 2 may indicate the cardiac cycle information and may provide the associated canonical images $X_c$ which will be included in set $W_n$.

In this scenario, cyclical canonical view trainer 115 may receive as input general frames $Y_m$, their approximate transformations $Z_m$ as generated by orientation neural network 15, and their associated cardiac cycle timing n, and may be trained to generate a set of summary images $W_n$ in a canonical view at desired times n. The optimization is:

$$\text{Loss} = \text{loss}(CC_n, W_n) \qquad (10)$$

where $CC_n$ is the output of the cyclical canonical view neural network 110 as it is being trained.

Cyclical canonical view trainer 115 may generate trained cyclical canonical view neural network 110 for navigator 100 using any appropriate neural network, such as a fullyconvolutional network, an encoder-decoder type of network or a generative adversarial network.

As illustrated in FIG. 9B to which reference is now made, navigator 100''' may comprise trained orientation neural network 15, a set creator 112' for operation, a sufficiency checker 60', a result converter 40', trained cyclical canonical view neural network 110 and diagnoser 50.

In operation, non-sonographer 5 may operate probe 7 near the body part of interest over a period of time, at least long enough to cover the desired body part cycle (such as the cardiac cycle). The images from probe 7 may be provided to trained orientation neural network 15 to generate their associated transformations S(X) and to set creator 112' to generate the appropriate sets $Y_m$ and $Z_m$. Sufficiency checker 60' may check that sets $Y_m$ and $Z_m$ are large enough and may instruct result converter 40' to instruct user 5 either to orientate probe 7 in a desired way or to continue viewing at the current orientation. It will be appreciated that, in this embodiment, non-sonographer 5 does not have to hold probe 7 at exactly the canonical view and thus, the instructions that result converter 40' may provide may be coarser. Cyclical canonical view neural network 110 may generate the summary cyclical, canonical views $CC_n$ from the output of set creator 112'.

It will be appreciated that this embodiment may also be useful for non-cyclical body parts, particularly for when user 5 may hold probe 7 unsteadily. In this embodiment, each set may have only one or two images therein.

Figure 10A:
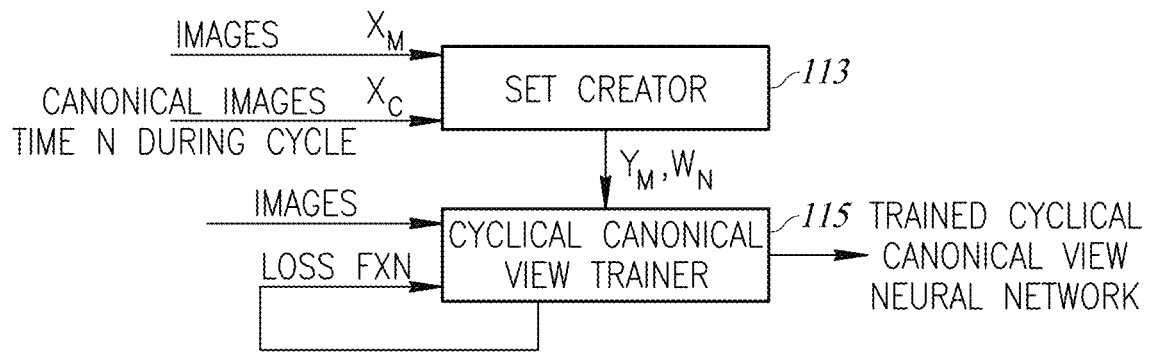
FIGS. 10A and 10B are schematic illustrations of the elements of an alternative embodiment to the navigator of FIGS. 9A and 9B at training and in operation, constructed and operative in accordance with the present invention.
Figure 10B:
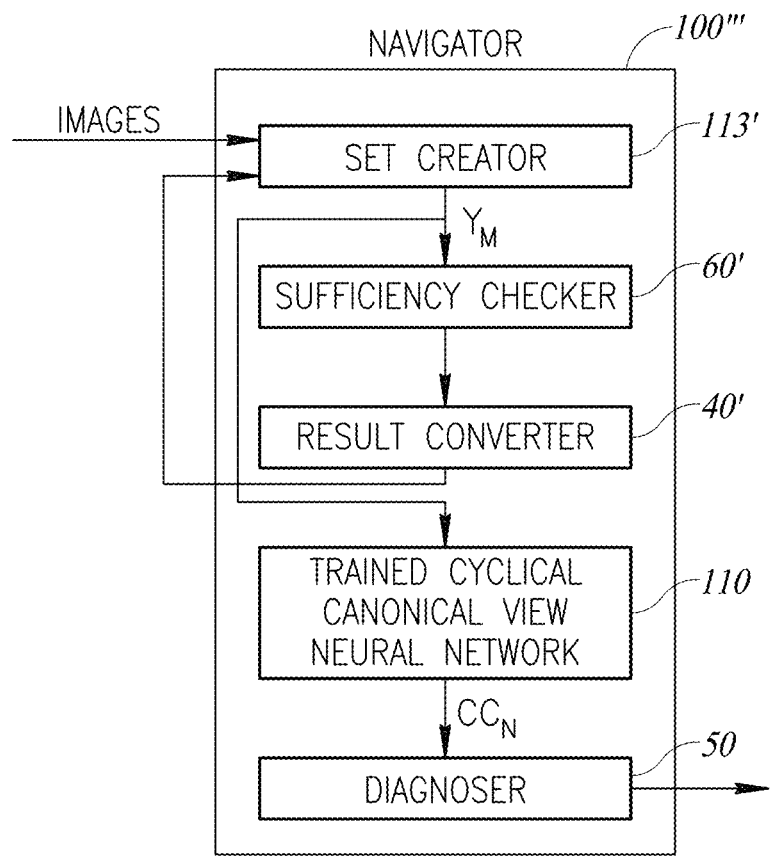

Applicants have further realized that neural networks can also be trained without the transformation information produced by trained orientation neural network 15. This is shown in FIGS. 10A and 10B, which illustrate a system similar to that of FIGS. 9A and 9B, but without trained orientation neural network 15. As a result, for training (FIG. 10A) a set creator 113 may create $Y_m$ from images $X_i$ and may create $W_n$ from canonical images $X_c$ at times n. Cyclical canonical view trainer 115 may generate cyclical canonical view neural network 110 using equation (10).

At runtime (FIG. 10B), a set creator 113' may create $Y_m$ from images $X_i$ and cyclical canonical view neural network 110 may generate the summary views $CC_n$.

It will be appreciated that the present invention may provide a navigator for non-sonographers to operate a mobile ultrasound machine without training and without any additional hardware other than the ultrasound probe. Thus, the navigator of the present invention receives ultrasound images as its only input. It will further be appreciated that this may enable non-sonographers to perform ultrasound scans in many non-conventional scenarios, such as in ambulances, in the battlefield, at urgent care facilities, nursing homes etc.

Moreover, the present invention may be implemented in more conventional scenarios, such as part of conventional machines used in hospital or clinic environments, which may also be implemented on carts.

Unless specifically stated otherwise, as apparent from the preceding discussions, it is appreciated that, throughout the specification, discussions utilizing terms such as "processing," "computing," "calculating," "determining," or the like, refer to the action and/or processes of a general purpose computer of any type such as a client/server system, mobile computing devices, smart appliances or similar electronic computing device that manipulates and transforms data represented as physical, such as electronic, quantities within the computing system's registers and/or memories into other data similarly represented as physical quantities within the computing system's memories, registers or other such information storage, transmission or display devices.

Embodiments of the present invention may include apparatus for performing the operations herein. This apparatus may be specially constructed for the desired purposes, or it may comprise a general-purpose computer or a client/server configuration selectively activated or reconfigured by a computer program stored in the computer. The resultant apparatus when instructed by software may turn the general purpose computer into inventive elements as discussed herein. The executable instructions may define the inventive device in operation with the computer platform for which it is desired. Such a computer program may be stored in a computer accessible storage medium which may be a non-transitory medium, such as, but not limited to, any type of disk, including optical disks, magnetic-optical disks, read-only memories (ROMs), volatile and non-volatile memories, random access memories (RAMs), electrically programmable read-only memories (EPROMs), electrically erasable and programmable read only memories (EEPROMs), magnetic or optical cards, Flash memory, disk-on-key or any other type of media suitable for storing electronic instructions and capable of being coupled to a computer system bus.

The processes and displays presented herein are not inherently related to any particular computer or other apparatus. Various general-purpose systems may be used with programs in accordance with the teachings herein, or it may prove convenient to construct a more specialized apparatus to perform the desired method. The desired structure for a variety of these systems will appear from the description below. In addition, embodiments of the present invention are not described with reference to any particular programming language. It will be appreciated that a variety of programming languages may be used to implement the teachings of the invention as described herein.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A portable computing device for a mobile ultrasound unit having an ultrasound probe, the device comprising:
   a trained orientation neural network to receive a non-canonical image of a body part from said mobile ultrasound unit and to generate a transformation associated with said non-canonical image, said transformation transforming from a position and rotation associated with a canonical image to a position and rotation associated with said non-canonical image; and
   a result converter to convert said transformation into orientation instructions for a user of said probe and to provide and display said orientation instructions to said user to change the position and rotation of said probe.

2. The device according to claim 1 and comprising a trainer to train said orientation neural network using said canonical image together with non-canonical images taken around said canonical image and transformations to positions and rotations in space associated with said non-canonical images from said canonical image.

3. The device according to claim 2 and wherein said trainer comprises a training converter to receive inertia measurement unit (IMU) data during training sessions from an IMU mounted on a training probe, said IMU data providing said positions and rotations associated with said non-canonical images and said canonical image, and to convert said positions and rotations to transformations from said position and rotation associated with said canonical image to said position and rotation associated with said non-canonical images.

4. The device according to claim 2 and wherein said trainer comprises an untrained orientation neural network and a loss function to train said untrained orientation neural network, said loss function to reduce a distance between a calculated transformation produced by said untrained orientation neural network and a ground truth transformation for each non-canonical image.

5. The device according to claim 4 wherein said loss function additionally includes a probability to constrain said calculated transformation to one of a plurality of different canonical orientations.

6. The device according to claim 1 wherein said canonical image is one of a plurality of canonical images.

7. The device according to claim 1 and also comprising a diagnoser to make a diagnosis from a final image generated by said probe when viewing said canonical image.

8. The device according to claim 1 and wherein said device is implemented on one of: a smartphone, a tablet, a laptop, a personal computer, and a smart appliance.

9. The navigator according to claim 1 and also comprising:
    a set creator to receive a multiplicity of transformations from said trained orientation neural network in response to images from said probe and to generate sets of images and their associated transformations;
    a sufficiency checker to determine when enough sets have been created; and
    a trained cyclical canonical view neural network to generate a set of summary cyclical canonical images showing changes in said body part during a body part cycle.

10. The navigator according to claim 9 and also comprising a cyclical canonical view trainer to train an untrained cyclical canonical view neural network with said sets of images, their associated transformations, and their associated summary cyclical canonical images at each point in said body cycle.

11. The navigator according to claim 9 wherein said body part cycle is a cardiac cycle.

12. The navigator according to claim 9 wherein each set has a single element therein.

13. A method for a mobile ultrasound unit having an ultrasound probe, implemented on a portable computing device, the method comprising:
    receiving a non-canonical image of a body part from said mobile ultrasound unit and generating, using a trained orientation neural network, a transformation associated with said non-canonical image, said transformation transforming from a position and rotation associated with a canonical image to a position and rotation associated with said non-canonical image; and
    converting said transformation into orientation instructions for a user of said probe and providing and displaying said orientation instructions to said user to change the position and rotation of said probe.

14. The method according to claim 13 and comprising training said orientation neural network using said canonical image together with non-canonical images taken around said canonical image and transformations to positions and rotations in space associated with said non-canonical images from said canonical image.

15. The method according to claim 14 and wherein said training comprises receiving inertia measurement unit (IMU) data during training sessions from an IMU mounted on a training probe, said IMU data providing said positions and rotations associated with said non-canonical images and said canonical image, and converting said positions and rotations to transformations from said position and rotation associated with said canonical image to said position and rotation associated with said non-canonical images.

16. The method according to claim 14 and wherein said trained mapping neural network comprises a loss function to ensure that changes in the motion of said probe generate small motions on said displayable map, that distances between images be similar to the distance between map locations and that optimal paths between one canonical image to another be straight, constant speed trajectories.

17. The method according to claim 16 wherein said loss function additionally includes a probability to constrain said calculated transformation to one of a plurality of different canonical orientations.

18. The method according to claim 13 wherein said canonical image is one of a plurality of canonical images.

19. The method according to claim 13 and also comprising making a diagnosis from a final image generated by said probe when viewing said canonical image.

20. The method according to claim 13 and wherein said portable computing device is one of: a smartphone, a tablet, a laptop, a personal computer, and a smart appliance.

21. The method according to claim 13 and also comprising:
    receiving a multiplicity of transformations from said trained orientation neural network in response to images from said probe and generating sets of images and their associated transformations;
    determining when enough sets have been created; and
    generating, using a trained cyclical canonical view neural network, a set of summary cyclical canonical images showing changes in said body part during a body part cycle.

22. The method according to claim 21 and also comprising training an untrained cyclical canonical view neural network with said sets of images, their associated transformations, and their associated summary cyclical canonical images at each point in said body cycle.

23. The method according to claim 21 wherein said body part cycle is a cardiac cycle.

24. The method according to claim 21 wherein each set has a single element therein.

* * * * *